(12) United States Patent
Prozzo et al.

(10) Patent No.: US 6,670,613 B2
(45) Date of Patent: Dec. 30, 2003

(54) SYSTEM AND METHOD FOR SPECTRAL ANALYSIS

(75) Inventors: Christopher D. Prozzo, Athens, VT (US); Allan McLane, Jr., Marlboro, VT (US)

(73) Assignee: Bacharach, Inc., New Kensington, PA (US)

( * ) Notice: Subject to any disclaimer, the term of this patent is extended or adjusted under 35 U.S.C. 154(b) by 207 days.

(21) Appl. No.: 09/842,431

(22) Filed: Apr. 26, 2001

(65) Prior Publication Data

US 2001/0045521 A1 Nov. 29, 2001

Related U.S. Application Data

(60) Provisional application No. 60/200,678, filed on Apr. 28, 2000.

(51) Int. Cl.[7] .................................................. G01J 5/08
(52) U.S. Cl. ........................................ 250/345; 250/343
(58) Field of Search ................................. 250/345, 343, 250/338.1, 336.1

(56) References Cited

U.S. PATENT DOCUMENTS 5,610,398 A  *  3/1997  Anderson et al. ...... 250/339.12

* cited by examiner

*Primary Examiner*—David Porta
*Assistant Examiner*—Christine Sung
(74) *Attorney, Agent, or Firm*—Webb Ziesenheim Logsdon Orkin & Hanson, P.C.

(57) ABSTRACT

A method and system for identifying and calculating the percentages of gases, such as the automotive and other commercial refrigerant gases, in a gas mixture using infrared spectroscopy is disclosed. The novel system is compact, relatively inexpensive and has greater accuracy than those systems of the prior art.

2 Claims, 1 Drawing Sheet

SYSTEM AND METHOD FOR SPECTRAL ANALYSIS

REFERENCE TO RELATED APPLICATION

This application is based on a provisional application Serial No. 60/200,678 which was filed on Apr. 28, 2000.

FIELD OF THE INVENTION

This invention relates to a system and method for identifying vapors and gases, particularly for identifying automotive and commercial refrigerants using infrared spectroscopy; and, which may also include an innovative system for measuring, by direct means, any percentage of air or other contaminant that may be present.

BACKGROUND OF THE INVENTION

It has been found that certain chlorine-containing fluorocarbons which have commonly been used in refrigerants can damage the ozone layer when released into the atmosphere. This finding has led to the replacement of these damaging fluorocarbons. As the ozone damaging hydrofluorocarbons are removed and new non-damaging fluorocarbons are used, it becomes important to be able to identify and keep segregated the various types of refrigerants. Increased government regulations of the fluorocarbons in the United States adds to the responsibility of the refrigerant service facilities, such as automotive repair facilities, which handle refrigerants.

In the automotive field, chlorine-containing refrigerants known as R12 ($CF_2Cl_2$), R22 ($CHF_2Cl$) and various blends have been used as automotive and home air conditioning refrigerants. The tetrafluoroethanes and pentafluoroethane, i.e., R134A ($CH_2F$—$CF_3$), R134 ($CHF_2$—$CHF_2$), R125 ($CHF_2CF_3$) have been found to be non-ozone damaging refrigerants and are presently being recommended and used in automobiles. Older cars may still be using R12 as a refrigerant. Because of the cost involved in converting existing automotive hardware to handle R134A, existing automobile owners may elect to continue using their prior refrigerant. However, because of government regulation, chlorine-containing R12 will no longer be acceptable in new cars. R22, a home air conditioning refrigerant which has been used, as a replacement for R12, because of its lower cost, will also not be acceptable for use as an automobile refrigerant in new automobiles.

It is possible that in an automobile's refrigerant system, as well as in the storage tanks of auto service centers, that a mixing of the above materials may take place. Because of the dangers associated with certain of the automotive refrigerants, as well as increasing government regulation, it is desirable to identify the individual refrigerant gases in both the automotive systems and storage facilities in order to maintain separate and pure stores of these materials. If a storage tank of refrigerant gases becomes contaminated, it should not be used for refiling an automotive refrigerant system.

In commercial air conditioning/refrigeration installations, there are approximately 25–35 different combinations of commercial refrigerants which are commonly used. As stated previously, certain commercial automotive refrigerants are ozone damaging. In addition, certain commercial refrigerants may damage the elastomeric seals used and may be incompatible with the lubricants used in a system designed for the new commercial refrigerants. Because of the wide variety of refrigerants utilized in the field, it is possible that more than one refrigerant is inadvertently present in a particular commercial refrigeration system and/or refrigerant storage tank. Thus, it is absolutely necessary to be able to identify all materials present in the refrigerant system before it is used commercially.

One method which has been used to identify gases is infrared spectroscopy. Most gases absorb infrared energy at specific wave lengths in the spectrum and, in many cases, at multiple points in the infrared spectrum. Infrared spectroscopy has been used to observe the phenomenon and identify particular gases. Traditional infrared spectroscopy equipment and methods, however, are not practical for field use at installations such as a local automotive repair facility because of cost, size, and their fragility. Existing infrared spectroscopy units, designed for laboratory use, are inappropriate for rigorous "unclean" environments such as that found in a local automotive repair facility. They also fail to meet the requirements of a portable device for transport and operation at a particular commercial establishment having commercial refrigerant systems.

In U.S. Pat. No. 5,610,398, whose disclosure is incorporated herein by reference thereto, a single infrared light source is used to determine the presence of multiple vapor gases in a refrigerant sample. Specifically, the infrared light source illuminates a refrigerant sample which has been placed in a test area (a so-called gas cell). The test area is physically located between the infrared light source and a plurality of infrared detectors. The infrared detectors receive the infrared light after it passes through the refrigerant sample. Each of the infrared detectors is sensitive to a different predetermined wavelength range of infrared light. Each of the infrared detectors is adapted to output a separate electrical signal corresponding to the infrared light received in its respective wavelength range.

Once a refrigerant sample is illuminated by an infrared light source and the plurality of infrared detectors receives infrared light passing through the refrigerant sample, and the resultant electrical signals are amplified and filtered, a processor reads the output electrical signals and determines whether the electrical output signals correspond to a particular refrigerant. The results of this determination are then displayed on an output device. This prior art system is shown in FIG. 1.

Another characteristic of this prior art system lies in the manner in which air is determined in the refrigerant system. Specifically, in U.S. Pat. No. 5,610,398, a multichannel non dispersive infrared sensor is calibrated to measure the amounts of each refrigerant (one per channel) in units of % by volume vs. optical absorbency. When a sample is introduced to the sensor, the optical absorbency of each channel is measured. Using the optical absorbency, the percent by volume is computed by looking into the calibration curves (previously prepared using known sample concentrations). The computed percentages by volume of each channel are then added together, if the total is less than 100%, the balance is called air, even though it could be some other substance. Air is never measured by direct means. The percent by weight is then computed by multiplying the percent by volume of each component by its known molecular weight and re-computing the percent of each component based on their fraction of the total weight×percentage volume of the sum. Since air is not considered a contaminant, it is left out of the sum when computing the refrigerant percent by weight. The percents by weight of the refrigerants by definition will always add up to 100% even if the air percent by weight is not zero.

OBJECTS OF THIS INVENTION

It is an object of this invention to provide a method and system for identifying automotive and other commercial refrigerants using infrared spectroscopy that is compact, relatively inexpensive, and more accurate than any in the prior art.

SUMMARY OF THE INVENTION

Figure 1:
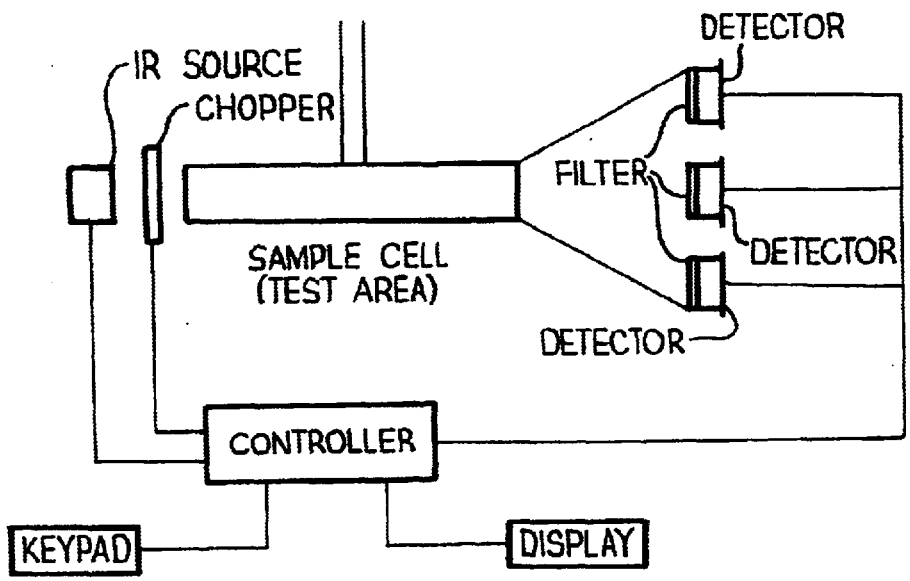
FIG. 1 is a schematic of a prior art system for spectral analysis.
Figure 2:
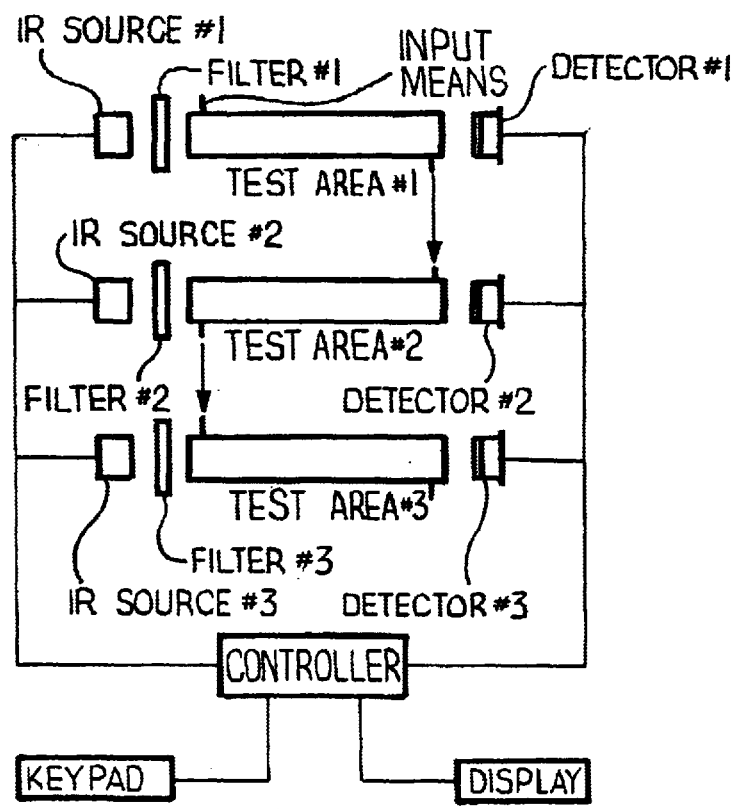
FIG. 2 is a schematic of a system for spectral analysis according to the present invention.

The objects are accomplished by using a plurality of sources of infrared light, each projecting light through filters to provide a predetermined wavelength range of infrared light, which is then projected through an equal number of separate test areas or gas cells and then to an equal number of detectors. The system of this invention is shown in FIG. 2.

Alternatively, the filters can be placed following the test areas i.e., between the test areas and the detectors. In either case, a different predetermined wavelength range of infrared light, each range corresponding to a different component in the test sample, is projected onto each detector.

Using this basic system, the light sources are much smaller and of significantly lower intensity than the single source of the prior art, consume less energy; require less space and are much less expensive than the single source systems of the prior art.

Furthermore, the system of this invention (and those of the prior art) can include an innovative system for measuring the percentage of air by direct means. Specifically, the infrared detector senses the infrared absorbance of the impinging gas as proportional to the number of molecules in the gas and the path length through which the gas is measured. The volume occupied by a gas is proportional to the number of molecules and their absolute temperature and absolute pressure. If an infrared sensor is calibrated in units of percent by volume and subsequent measurements are then made at different temperatures and pressures, the results will err proportionally with the percent of difference of absolute pressure and absolute temperature between the calibration and the measurement. The pressure variation with altitude and weather in the United States is enough to skew the measured percent by volume by several percent. Because the percent by volume of air is simply 100% minus the sum of the refrigerants' percentages by volume, this error is translated directly to the percent by volume of air.

Upon conversion to percent by weight, the refrigerant sum is forced to equal 100% so the effect on the refrigerant is hidden. The effect on the air is reduced in the conversion to percent by weight but still renders the results unusable over the normal altitude variation of US cities. For this reason, the prior art instruments employed a means of compensating for the effect of altitude by having the instrument user enter the altitude of their location into the unit. A correction is then applied to the percent by volume numbers based on the percent difference between the absolute pressure at calibration and a standard absolute pressure at the altitude entered by the user. This is sufficient to bring the unit into reasonable accuracy barring severe weather conditions or wide temperature swings (unless a temperature compensation is also applied).

If one calibrates an infrared gas analyzer to percent by volume, it is being calibrated to a second order stimulus. This would be similar to making an ammeter out of a voltmeter by calibrating it to amps by passing known current through a resistor and recording the voltage across it at several different currents. This results in a response curve of volts versus amps. The operator then measures the current through a resistor in this instrument. If that resistor has the same value that the instrument was originally calibrated, then the results will be accurate. If it has any other value, then the results will be in error in proportion to the difference in the value used to calibrate and that used at the time of the measurement. Also, if the resistor is the same, but the temperatures are very different, the results will also be in error since the resistance has a temperature dependence.

One way to control this problem would be to issue a fixed temperature-stable resistor that the customer must use by placing it in series with the circuit in which the current is being measured. This is precisely how a multi meter works. When you switch to amps, voltage is measured across an internal "shunt" resistor, through which the current is passed, and related to amps based on the voltage calibration and the resistance value of the shunt. This method of calibrating an ammeter would be equivalent to controlling the absolute pressure in the gas sensor so that it is always the same during the measurement of gas composition. This would be a cost prohibitive approach.

Recognizing that the detector or sensor's first order response is to the absolute number of molecules (assuming a fixed path length) and not the percent by volume, we have employed measurement algorithms based on calibrations of the number of moles of gas in the absolute concentration vs. optical absorbance in milligrams or milligrams per liter. With the addition of a temperature and pressure sensor, the total number of moles of all gases together can be directly determined using the ideal gas law. Subtracting the number of moles, determined by optical absorbance, from the total number of moles, determined by pressure, temperature and volume, leaves the number of moles of any 'unknown', such as air, that may be present in the sample. One can then report the concentration in any other units including percent by volume or percent by weight using simple mathematics.

Specifically, the innovative system involves (1) calibrating a multi-channel non-dispersive infrared sensor to measure refrigerants (one per channel) in units of moles vs. optical absorbency;

(2) introducing a sample to the sensor and (3) measuring the optical absorbency of each channel as well as the absolute pressure and temperature;

(4) using the optical absorbency and the calibration curves, determining the number of moles;

(5) computing then the weight of each gas in the sample chamber by multiplying the moles by the molecular weight of the gas (crosstalk correction is applied here);

(6) computing the percent by weight of each component by their fraction of the sum of the weights of all components;

(7) determining the total number of moles of all gases contained in the test area using the temperature, pressure and the volume of the sensor cell;

(8) subtracting the sum of moles of all components determined optically in (4) from the total number of moles determined in (7);

(9) if the sum is less than the total in (8), the difference is the number of moles of an unknown component such as air;

(10) determining the percent by volume of the unknown by the same method as determined its mole fraction, regardless of what it is. The percent by weight is computed by applying a molecular weight to the mole fractions, assuming the unknown is air, use its molecular weight, and compute the fraction of the sum of all the components, applying their individual molecular weights, respectively.

The advantages of an instrument using this system are numerous:

First, the instrument is calibrated in its native units and the percentages by weight are then based on direct measurement and are not influenced by temperature or pressure since the mole fraction of a component is not affected by temperature or pressure.

Second, the presence of an unknown is determined by mole fraction (requiring pressure and temperature sensors) not by percentage by volume, and is, therefore, not influenced by altitude, atmospheric conditions or temperature.

Third, the percentages by weight of the refrigerants are not derived from percentages by volume; and percentage by weight of the unknown is also not derived from percentage by volume, but rather from mole fraction and an assumed molecular weight.

The advantages of the system of the present invention over the system of the prior art (U.S. Pat. No. 5,610,398) are apparent from the following comparison of algorithms:

Prior Art

1. Measure optical absorbance on channels x, y, z
2. Volume % x=cal_curve_x(absorbance_x) (accuracy affected by pressure and temperature)
(repeat for y and z)
3. Apply crosstalk correction
4. Air volume %=100−x%−y%−z% (error from 2, goes into air volume %)
5. Air weight %=Air volume % times Air molecular weight divided by the sum of x,y,z volume %s times their molecular weights.

Method of Invention

1. Measure optical absorbance on channels x,y,z
2. Moles/liter x=cal_curve_x(absorbance_x) (accuracy affected by pressure and temperature)
(repeat for y and z)
3. Apply crosstalk correction
4. compute total number of moles in test area using pressure and temperature and ideal gas law $N_{total}=PV/RT$ where N is the total number of moles in volume V at temperature T and Pressure P (R being the gas constant)
5. Compute the number of moles of AIR $N_{air}=N_{total}-N_x-N_y-N_z$
6. Air weight %=$N_{air}$ times molecular weight of air divided by the sum of $N_x$, $N_y$ and $N_z$, each N times the molecular weight of X, Y and Z.

In the following example, the operation of the novel system and a sample computation are provided:

EXAMPLE

1. A mixture of refrigerants R12, R134A and R22, and AIR is caused to flow through the gas cells (each having a volume of 1 cubic centimeter) of three optical sensors, each having optical filters designed to pass wavelengths at approximately 11.25 $\mu$m, 10.20 $\mu$m and 12.5 $\mu$m, respectively.

2. The total number of moles in the gas cells is determined by measuring pressure and temperature of the flowing gas mixture using solid state sensors.

Pressure=14.75 PSIA and
Temperature=318 degK.$N_{Total}$=PV/RT=(14.753 psia*|cc)/(1206*318 degK)=38.46 micro moles.

3. The optical absorbance is determined for each gas cell or test area utilizing a previously stored measurement determined using clean AIR.

4. The number of moles of each component is computed using predetermined calibration curves prepared as moles vs. optical absorbance.

5. Determine the number of moles of AIR by subtracting the sum of moles found in step (4) from the total determined in step (2). $N_{air}$=38.46−(30.0+4.0+1.0)=3.46 micro moles.

6. The mole fraction of all components is now obtainable. By definition, the percent by volume and the mole fraction are the same. The percent by weight is simply determined by multiplying the mole fractions by their respective molecular weights and recomputing the weight percentages of components from the sum of the weights.

What is claimed is:

1. A system for identifying and analyzing the amounts of individual refrigerants in a mixture of refrigerant components and contaminants comprising:

(1) a plurality of test areas or gas cells adapted to contain samples of said mixture;

(2) a plurality of infrared light sources adapted to project light through each of said cells;

(3) a plurality of light filters placed either before or after said cells containing said samples, each filter adapted to provide a predetermined wavelength range of infrared light corresponding to one of the refrigerant components in said mixture;

(4) a plurality of light detectors calibrated to sense the infrared absorbance of the impinging light and adapted to provide a signal corresponding to the percentage by volume of each of the individual refrigerant components of said mixture;

(5) means to measure pressure and temperature of samples being analyzed, wherein said pressure is measured relative to atmospheric pressure; and (6) means for determining the presence and amount of a contaminant which is not detected optically, as a function of the measured pressure and temperature of the samples being analyzed.

2. The system of claim 1, wherein the contaminant is air.

* * * * *